(12) United States Patent
Smith et al.

(10) Patent No.: US 6,661,000 B2
(45) Date of Patent: Dec. 9, 2003

(54) METHOD FOR MEASURING ABSORBED AND INTERSTITIAL FLUIDS

(75) Inventors: Michael P. Smith, Tulsa, OK (US); Robert J. Pottorf, Houston, TX (US); Gary G. Gray, Bellaire, TX (US); Maxim O. Vityk, The Woodlands, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 0 days.

(21) Appl. No.: 10/316,725

(22) Filed: Dec. 11, 2002

(65) Prior Publication Data
US 2003/0106995 A1 Jun. 12, 2003

Related U.S. Application Data

(60) Provisional application No. 60/340,878, filed on Dec. 12, 2001.

(51) Int. Cl.⁷ .................................. H01J 37/26
(52) U.S. Cl. ......................................... 250/282
(58) Field of Search ................... 250/282, 281

(56) References Cited

U.S. PATENT DOCUMENTS

| 2,177,139 A | 10/1939 | Horvitz | 62/175.5 |
| 2,183,964 A | 12/1939 | Horvitz | 23/232 |
| 2,192,525 A | 3/1940 | Rosaire | 23/232 |
| 2,261,764 A | 11/1941 | Horvitz | 23/232 |
| 2,287,101 A | 6/1942 | Horvitz | 23/232 |
| 2,324,085 A | 7/1943 | Horvitz | 23/232 |
| 2,470,401 A | 5/1949 | Horvitz | 23/230 |
| 3,033,287 A | 5/1962 | Bond | 166/4 |
| 4,736,792 A * | 4/1988 | Brown et al. | 166/252 |
| 4,898,831 A | 2/1990 | Smith | 436/32 |
| 4,916,314 A | 4/1990 | Smith | 250/307 |
| 4,965,209 A | 10/1990 | Smith | 436/32 |
| 5,224,658 A | 7/1993 | Smith | 241/27 |
| 5,241,859 A | 9/1993 | Smith | 73/153 |
| 5,286,651 A | 2/1994 | Smith | 436/32 |
| 5,328,849 A | 7/1994 | Smith | 436/32 |

OTHER PUBLICATIONS

Fontana, John V. (1994) "Improvements in Soil, Interstitial Soil Gas, and Ground Water Sample Acquisition With Hydraulic Probe Driven Technologies for Near Surface Geochemical Exploration Surveys", AAPG Hedberg Res. Conf., Vancouver, Brit. Columbia, Canada, 4 pages.

Tissot, B. P. and Welte, D. H. (1984) "Petroleum Formation and Occurrence", 2nd Ed., Springer–Verlag, Berlin, p. 420.

* cited by examiner

Primary Examiner—Kiet T. Nguyen
(74) Attorney, Agent, or Firm—J. Paul Plummer

(57) ABSTRACT

A method for predicting hydrocarbon-bearing zones and estimating rock properties by analyzing fluids trapped in the pore spaces or adsorbed on the surfaces of rock samples. The trapped gases are removed under vacuum and analyzed by a mass spectrometer. Data peaks corresponding to petroleum constituent molecules provide an indication of presence and abundance of hydrocarbons. A decrease of the count rate over time is used to estimate permeability and other rock properties. Concentration ratios for selected constituents indicate oil quality and depth of the oil-water contact.

16 Claims, 12 Drawing Sheets

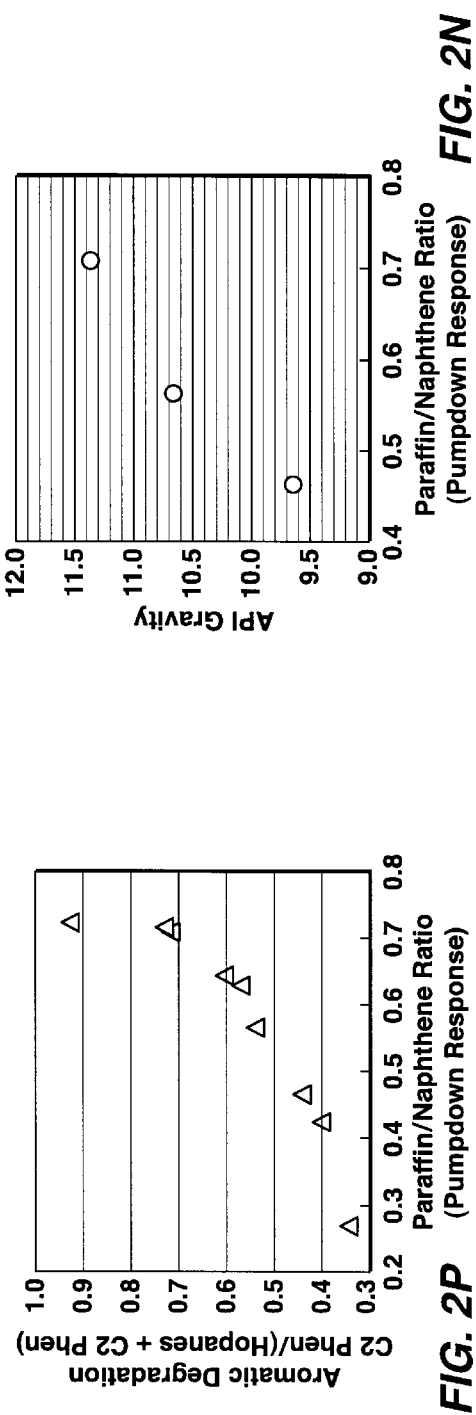
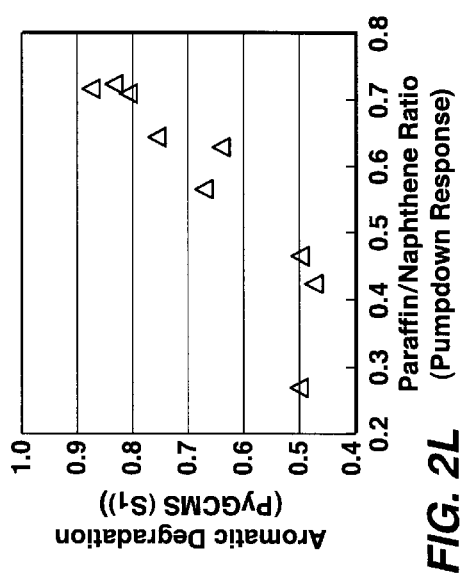
FIG. 2M  FIG. 2N  FIG. 2L  FIG. 2P

METHOD FOR MEASURING ABSORBED AND INTERSTITIAL FLUIDS

This application claims the benefit of U.S. Provisional Application No. 60/340,878 filed on Dec. 12, 2001.

FIELD OF THE INVENTION

This inventive method relates generally to the field of prospecting for hydrocarbons, and more particularly, to extraction and analysis of compounds adsorbed to the surfaces and present in the pore spaces of samples such as drill cuttings and drill cores.

BACKGROUND OF THE INVENTION

Fluid inclusion stratigraphy ("FIS") analysis methods have been known for more than ten years. The fluids that are analyzed in FIS analysis are trapped in tiny sealed enclosures in a sedimentary rock sample, and require some sort of physical deformation of the sample to release them. Subjecting the sample to a vacuum will not cause FIS gases to be released. The physical deformation is, most commonly, a mechanical crush or squeeze of the sample. Alternatively, a laser, an ion beam, or a tiny drill bit may be used to rupture at least one of the fluid-enclosing pockets in the sample.

In a typical FIS analysis, a sedimentary rock sample is crushed under vacuum and the trapped fluids that are released by the crush are analyzed, often with a mass spectrometer. When the sample or samples in the crush chamber are replaced, the chamber is pumped down again to the desired vacuum before crushing the new sample. This evacuation is necessary both to reduce background from the atmosphere and the previous sample and in order not to damage the mass spectrometer. In addition, the evacuation tends to pull out fluids trapped in the pore spaces or adsorbed onto grain surfaces of the new sample(s). These adsorbed and pore space gases are probably of origin different from that of the FIS gases which require crushing or squeezing to be released, and hence are considered a contaminant in FIS analysis that is either to be pumped off before the analysis begins or is subtracted as background from FIS results. The trapped FIS fluids (mostly gases when released under high vacuum) may be of ancient origin, which helps analysts understand formation and evolution of the subterranean formation. Equally or sometimes more usefully, the FIS results often exhibit anomalies that correspond to current hydrocarbon-bearing formations when the analysis is performed on rock chips obtained from well drilling or on outcrop samples. Either way, FIS analysis is useful in exploration and production of hydrocarbons.

Various traditional methods are the alternatives to FIS analysis to evaluate formation fluids from evidence obtained from well drilling or core samples. Some methods do this indirectly by providing estimates of pertinent rock properties. These methods include a variety of wire-line logging tools and formation testers. Porosity is either measured in core samples or more commonly estimated from logging tools using density, nuclear and acoustic properties. Permeability is estimated from core analysis or from nuclear magnetic resonance measurements. Formation fluid type (oil, gas, or water) is predicted from electrical resistivity measurements combined with other measurements from logging tools. Such indirect techniques can have limited reliability, which may lead to ambiguities in formation evaluation.

More direct techniques to evaluate rock properties and formation fluids while drilling also exist. These methods go by the general name of mud logging. Mud loggers describe the rock cuttings during drilling, use ultraviolet light to look for petroleum fluorescence, and monitor gas chromatographs to detect hydrocarbon gases from methane to pentane within drilling fluids. These more direct types of hydrocarbon detection also give variable results.

FIS analysis gives a fundamentally different type of information that is often needed to resolve uncertainties and ambiguities that arise from the above-identified traditional methods. Valuable as FIS analysis is, it suffers from the inherent drawback that what is analyzed may date back to distant, earlier times and may not accurately represent current formation conditions. It would be desirable to have a method that extracts more currently relevant information in statistically significant quantity. The present invention satisfies this need.

SUMMARY OF THE INVENTION

In one embodiment, the present invention is a method for petroleum exploration comprising the steps of obtaining one or more samples, which might be drilling cuttings or core or outcrop samples, from known surface or underground locations, then placing each sample under vacuum in the presence of a detector such as a mass spectrometer, using the mass spectrometer to analyze the composition and concentration of fluids released from interstitial cavities and pore spaces of the sample and also from surface adsorption, and predicting the presence and location of petroleum based on the measured concentration of petroleum indicator molecules.

In another embodiment, the present inventive method can be used to estimate rock properties such as permeability, the method comprising the steps of (a) placing a rock sample in an air-tight chamber connected to a vacuum pump and to a detector such as a mass spectrometer; (b) using the detector to measure the detection rate (ion current in the case of a mass spectrometer) as a function of elapsed time for at least one molecular constituent of the adsorbed and interstitial fluids released by the sample due to the reduced pressure and (c) comparing the response vs. time data from the unknown sample to similar data from samples with known values of the rock property, thereby estimating the rock property for the unknown sample.

In other embodiments, the present inventive method can be used to measure oil quality, or the location of the oil-water interface in a reservoir, by comparing measured concentrations of selected petroleum or non-petroleum constituent molecules.

BRIEF DESCRIPTION OF THE DRAWINGS

The present invention and its advantages will be better understood by referring to the following detailed description and the attached drawings in which:

FIGS. 2L, 2M, 2N and 2P illustrate tests of the validity of the Paraffin/Naphthene ratio from pumpdown data as an oil quality estimation tool;

The invention will be described in connection with its preferred embodiments. However, to the extent that the following detailed description is specific to a particular embodiment or a particular use of the invention, this is intended to be illustrative only, and is not to be construed as limiting the scope of the invention. On the contrary, it is intended to cover all alternatives, modifications and equivalents which are included within the spirit and scope of the invention, as defined by the appended claims.

DETAILED DESCRIPTION OF THE INVENTION

The present invention, which may be called the volatiles pumpdown technique or simply the pumpdown technique, enables the analyst to directly measure the composition of pore-filling fluids from samples such as rock chips (drill cuttings), cores, or from rocks otherwise obtained from the surface or subsurface. In preferred embodiments of the present invention, a mass spectrometer is used to analyze the residual interstitial fluids that are drawn from the sample by evacuation. The present inventive method employs actual rock samples and therefore is not subject to the problems of formation water chemistry or some of the drilling conditions that influence wire-line techniques. One or more samples are placed in an airtight, evacuated chamber. Under the influence of the vacuum, the volatile fluids in the samples are liberated (the "pumpdown" phase) and analyzed by the mass spectrometer. Current, commonly available mass spectrometers can scan 200 or more different molecular masses or compounds nearly simultaneously. If cutting samples are taken periodically as a well is being drilled, a profile can be made of the abundance of various compounds with depth down the drill hole. In this type of display, hydrocarbon-bearing zones have a high abundance of hydrocarbons and associated compounds whereas water-bearing intervals are generally devoid of such signals. Additionally, the strength of the detected signal through time within samples containing the same fluids is a function of certain rock properties of the sample, specifically porosity and permeability.

Figure 1:
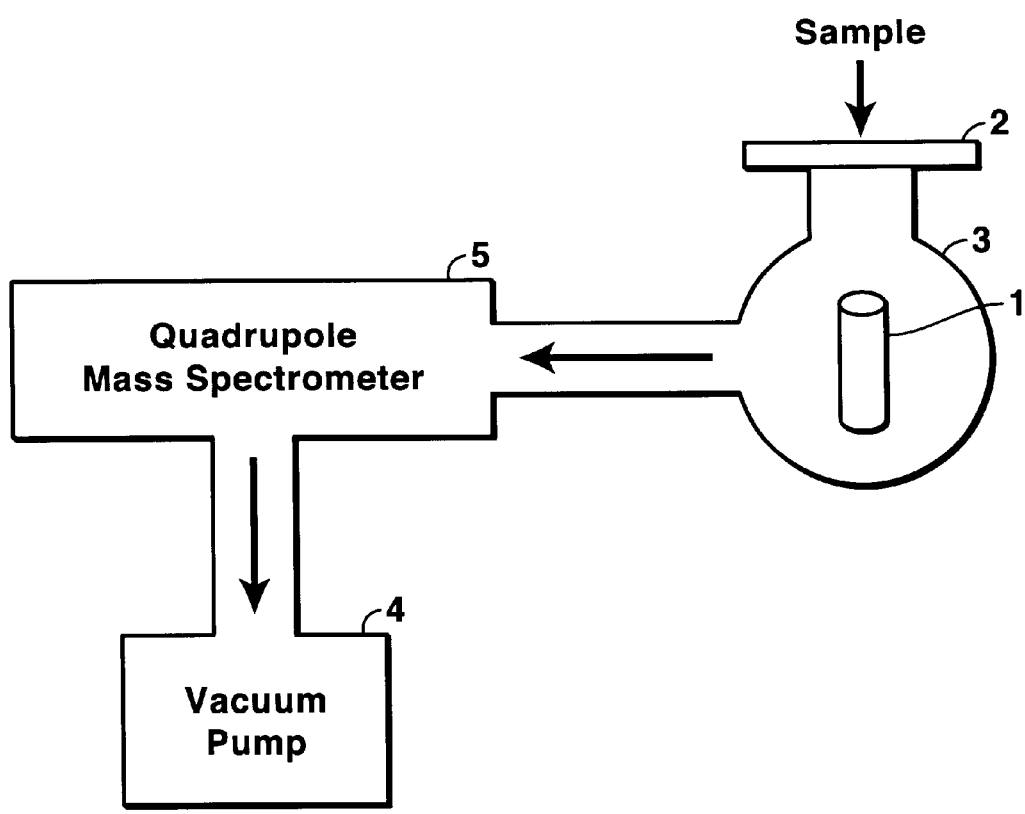
FIG. 1 is a general schematic of an analytical apparatus containing the main features needed for implementing the present inventive method.

FIG. 1 shows the general schematic of an analytical apparatus that may be used for practicing the present invention. The sample 1 is admitted through a valve 2 to a vacuum chamber 3 to which is connected a vacuum pump 4 and a measuring device such as a quadrupole mass spectrometer 5. The vacuum pump does not have to be connected to the system behind the mass spectrometer as long as it is connected to the system somewhere. The system must be evacuated to vacuum levels that sufficiently remove remnants of the previous sample and air admitted with the new sample, and at which the mass spectrometer will operate properly. In practice, the mass spectrometer operating limitations typically control when data collection can begin. Typically, the vacuum pump will continue to operate throughout the entire process. Regardless, some of the sample's interstitial and adsorbed gases ("pumpdown gases") will be unavoidably lost during the attainment of a vacuum level sufficient for measurement to be started. Because the concentration of pumpdown gases is small to begin with, much smaller than typical FIS concentrations, data gathering should not be delayed unnecessarily. However, continued operation of the vacuum pump is not necessary for most applications of the invention as long as the vacuum remains good enough to allow data collection notwithstanding sample insertion and the passage of time while measurements are made. The exception occurs when the invention is used to measure rock properties. As described below, in that instance where the decay of signal over time is what is measured, then continued pumping is an integral part of the process.

With regard to the preceding considerations relating to operating limitations of mass spectrometers, one concern is that the filament will burn out if the gas pressure is too high. The concern for the filament in a mass spectrometer relates to the concentration of ionizing gases. As long as the concentration or partial pressure of ionizing gases in the chamber is below a level determined by the particular mass spectrometer that is used, the total pressure of the gases in the chamber is not a factor as far as filament life is concerned (although total pressure, if too high, will affect the ionization and filtering functions). This can be an important consideration because all evacuating performed on the sample and before the detector is turned on reduces the count rates for the molecular masses of interest (along with the count rates for the masses of no interest) without yielding any data.

In some preferred embodiments of the present invention, pains are taken to eliminate possible sources of hydrocarbon contamination of the sample chamber. For example, vacuum pumps are selected that do not use oil as a lubricant or as part of their method of operation. Other possible sources of hydrocarbon contamination are O-rings and seals used to maintain the vacuum and any greases used in conjunction with them. Also, solvents are avoided for cleaning in favor of alternatives like soap and water followed by heat for drying. Notwithstanding the preceding, such oil elimination is not necessary for the present invention to work.

It is believed that adsorbed and interstitial gases are typically of more recent origin than the encapsulated FIS gases, and therefore may be more indicative of hydrocarbon presence or migration pathways as they exist today. However, experience shows that just as with fluid inclusions, old samples such as those from wells drilled years ago often still contain typical concentrations of hydrocarbons among their interstitial and adsorbed gas concentrations. This availability of libraries of samples from regions all over the world greatly extends the applicability of the present invention beyond its obvious value for analyzing cutting and core samples as a well is being drilled, with the results used for "real time" drilling decisions. The present inventive method proves to be particularly suited for accurately predicting fluid contacts such as the depth of the oil-water contact in an oil reservoir.

A mass spectrometer works by ionizing atoms or molecules and passing the ions in a beam through an electric field toward a collector/counter. The electric field is varied and a measurement taken at each value of the field, which corresponds to a unique value of the ratio m/z for the ion, where m is the mass (typically, in amu's, or atomic mass units) and z is the ionic charge in electronic charge units. Thus, m/z will equal m for singly ionized ions (which will predominate); m/z will equal m/2 for less prevalent doubly ionized ions, and so on. If one wishes to detect the water molecule, the largest peak will be at m/z=18. A smaller peak will be at m/z=9. Actually, because water is so abundant in almost any sample, these peaks overload the measuring equipment. Accordingly, one looks for a peak at m/z=20 corresponding to the water molecule consisting of hydrogen and the $O^{18}$ isotope of oxygen. From the known abundance of this isotopic variant of water (m=20) relative to normal water (m=18), the data can be adjusted to yield the actual water concentration. Oxygen also occurs as $O^{17}$ and accordingly the m/z=19 peak is an alternative.

Commonly used indicators for oils or wet gases, in order of increasing molecular mass, are (with m/z in parentheses) $C3^+$ (41), naphthenes (55), paraffins (57), and alkylated napthenes (97). Prevalence of molecules lighter than the preceding, such as methane (15) and ethane (30), tend to indicate gas. Some care must be taken in identifying mass spectrometer output peaks since, for example, m/z=55 may not be unique to the naphthene ion.

Figure 2B:
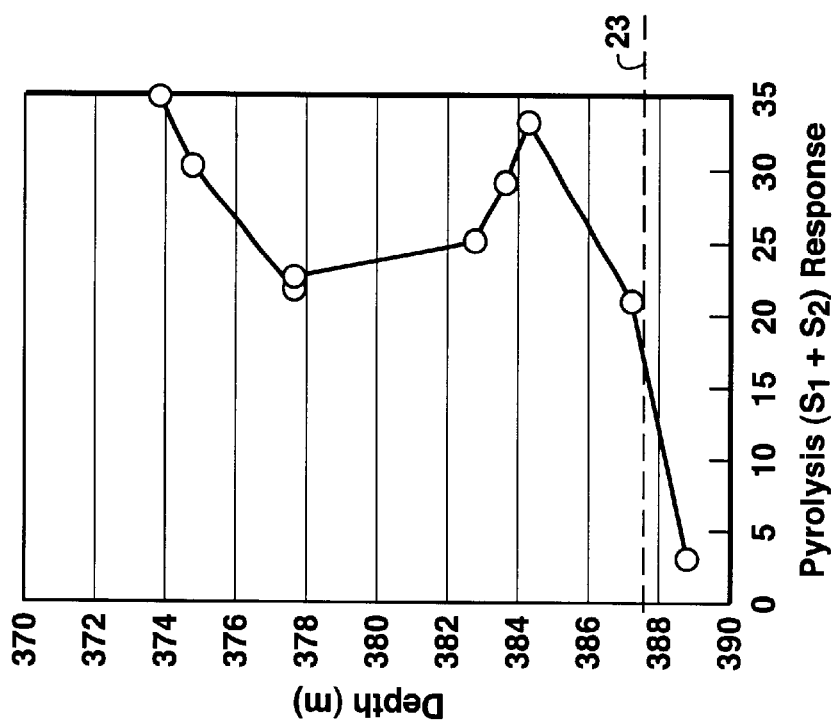
FIGS. 2A and 2B compare the present invention (FIG. 2A) to a conventional pyrolysis method (FIG. 2B) with respect to locating the oil-water contact depth.
Figure 2A:
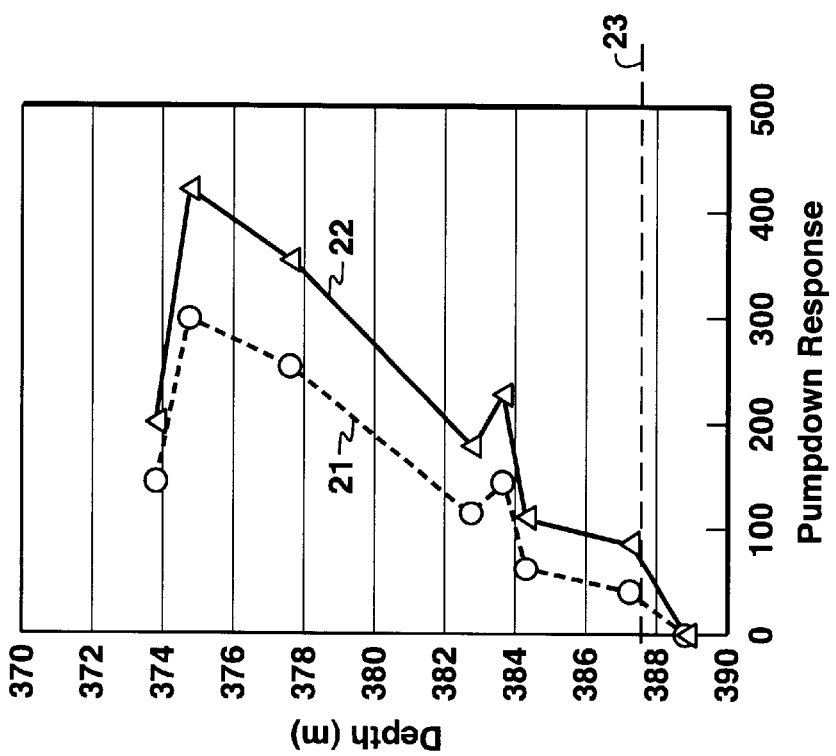

FIG. 2A shows pumpdown data from core samples obtained in the heavy oil area of Canada at depths from 374 m to 389 m below the surface. The points 21 represent the pumpdown response for naphthenes (m/z=55) and the points 22 the response for paraffins (m/z=57). The abrupt decrease of the response for both petroleum constituents to zero at a depth of 389 m strongly suggests that the oil-water contact occurs just above that depth. In fact, it is known to be at or near 387.2 m, indicated by dashed line 23 in FIG. 2A. FIG. 2B shows this same determination made by a known direct method of sample analysis called pyrolysis ($S_1+S_2$), which is more costly and time-consuming to use than is the present inventive method.

The term ($S_1+S_2$) refers to the fact that when a sample containing oil is pyrolyzed (heated), one group of hydrocarbons (the "$S_1$" peak) comes off at about 300° C. while the rest (the "$S_2$" peak) need a temperature on the order of 650° C. to be driven off. For purposes of determining the oil-water contact, i.e. distinguishing oil from water, the $S_1$ contents of the sample are combined with the $S_2$ contents, and that measured concentration is plotted on the horizontal axis of FIG. 2B. In FIG. 2A and drawings to follow that plot "pumpdown response", the scale and units should be considered arbitrary. The quantity plotted is derived from ion current measurement by the mass spectrometer, but scaling, normalization, and background correction vary with the application as the person of ordinary skill in the art will understand.

Figure 2C:
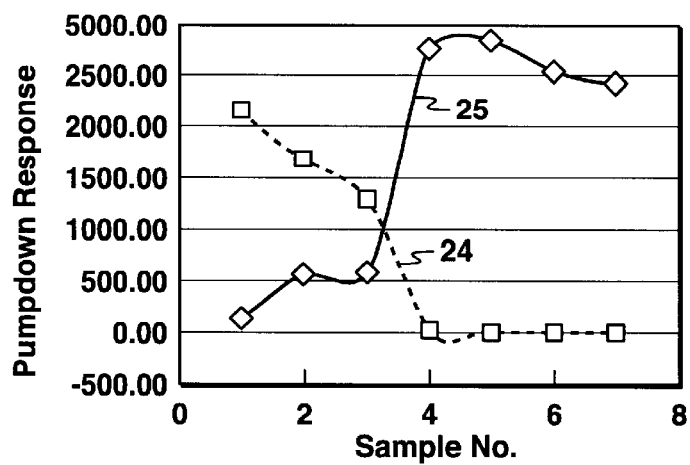
FIGS. 2C, 2D and 2E illustrate use of the present invention to distinguish oils of different quality.
Figure 2D:
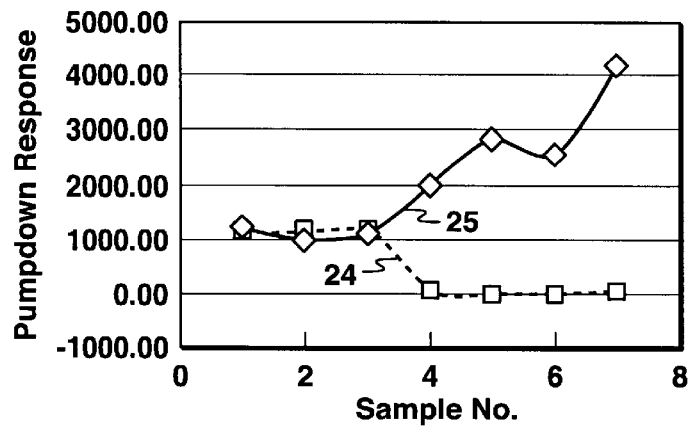
Figure 2E:
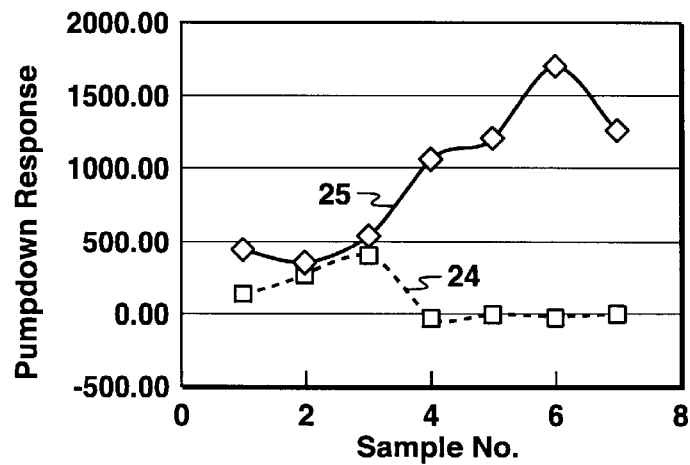

In addition to distinguishing between oil and water, the present inventive method can be used to distinguish between oils of different quality, i.e. oils of different API gravity and viscosity. FIGS. 2C, 2D and 2E illustrate use of the present inventive method on sandstone core samples to evaluate oil API gravity. In each experiment, samples 1, 2 and 3 are saturated with oil, and samples 4, 5, 6 and 7 are saturated only with water. In FIG. 2C, the oil is a heavy oil (API 11°), in FIG. 2D a normal oil (API 27°), and in FIG. 2E a light oil (API 41°). In each case, the (background corrected) pumpdown response is plotted for liquid hydrocarbon $C3^+$ (m/z= 41) denoted by 24 and water (m/z=19) denoted by 25. All three figures show an elevated $C3^+$ response for the oil saturated samples compared to the water saturated samples, and an elevated water response for the water saturated samples compared to the oil saturated samples. However, the heavy oil experiment (FIG. 2C) shows a crossover between the $C3^+$ and water curves with a pronounced departure between the two curves on either side of the crossover. For normal oil (FIG. 2D), a crossover barely occurs followed by virtually no departure to the left of the crossover. For light oil (FIG. 2E), there is no crossover and a slight reverse departure to the left. These crossover and departure characteristics are typical and may be used to estimate API gravity in particular and detect oil quality in general. If the samples were taken from varying depths from the same core, the crossover point can be used to pick the oil-water contact.

Figure 2F:
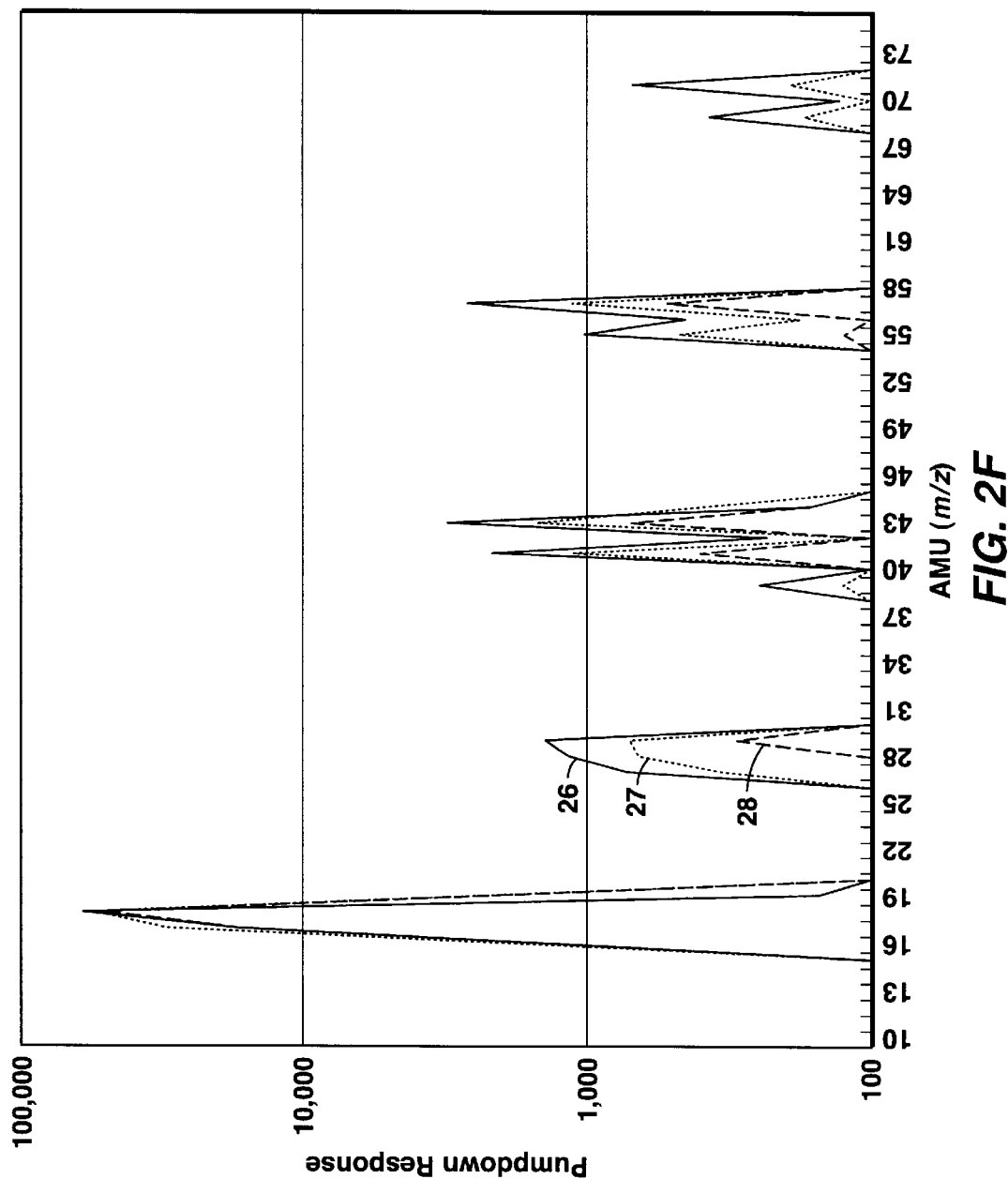
FIG. 2F illustrates an alternative way of using the present invention to distinguish oil quality differences, by comparing the pumpdown response for the full mass spectrum.

FIG. 2F illustrates another way to use the present inventive method to evaluate oil quality. In the figure, the pumpdown response for the full mass spectrum (after removal of statistically insignificant data) is plotted. Three rock samples are analyzed, each containing an oil of different density. A rock sample containing heavy oil (API 11°) is represented in FIG. 2F by 26; normal oil (API 27°) is 27; and light oil (API 41°) is 28. The spectra are characteristic of the oil densities, and their differences may be used to detect oil API gravity of an unknown sample.

Figure 2K:
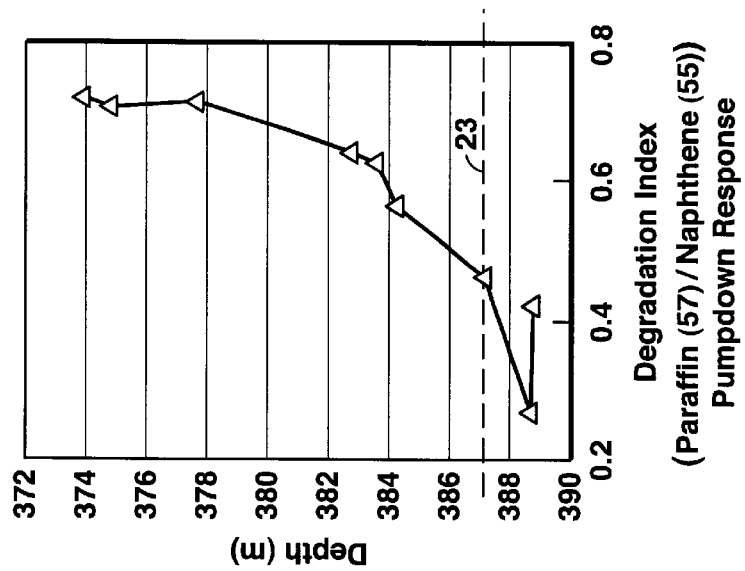
FIGS. 2I, 2J and 2K are plots of an oil degradation index vs. depth as determined by two conventional methods (FIGS. 2I and 2J) compared to the present invention (FIG. 2K)
Figure 2J:
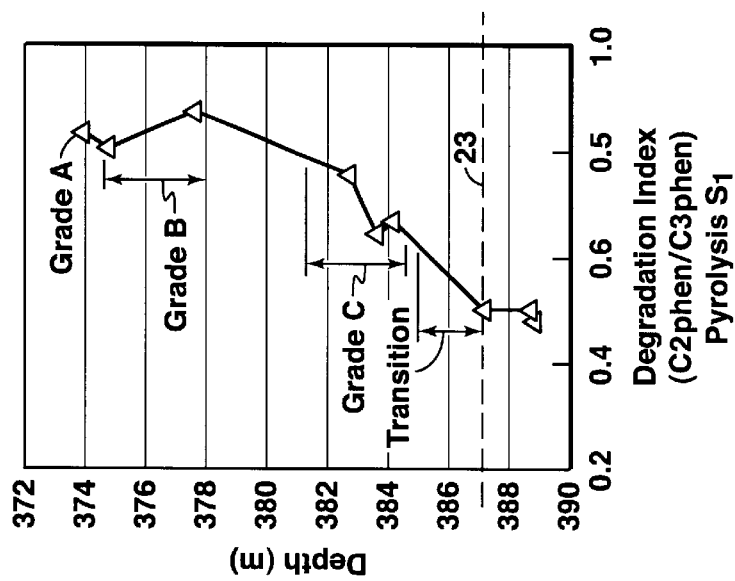
Figure 2I:
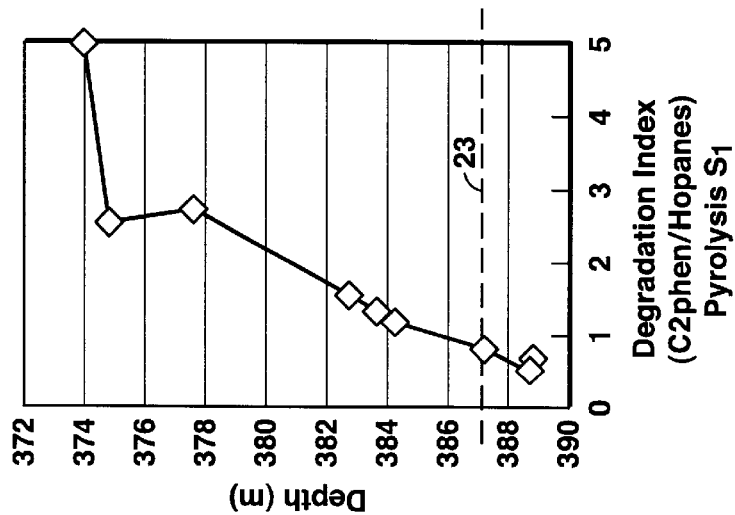

A known way to determine oil quality is to determine a "degradation index" by chemical analysis of a pair of petroleum constituent molecules chosen to be respectively more predominant at opposite ends of the quality spectrum (due to preferential reduction by biodegradation). Therefore, the ratio of the concentration of one of the constituents to the other yields a measure of oil quality called a degradation index. One such index is the ratio of C2phenanthrenes to Hopanes; another is the ratio C2phenanthrenes/C3phenanthrenes. (Hereinafter, the abbreviations C2phen and C3phen will be used.) In each case, a greater index value indicates a higher quality oil. A similar degradation index can be calculated using a pair of peaks in the pumpdown response spectrum. The ratio of paraffins (m/z=57) to naphthenes (m/z=55) is one preferred choice among other possibilities. (See *Petroleum Formation and Occurrence*, $2^{nd}$ Ed., by B. P. Tissot and D. H. Welte, Springer-Verlag, Berlin (1984) p. 420). In FIGS. 2I, 2J and 2K, the degradation index is plotted for core samples taken at the listed depths from the same core that yielded the data for FIGS. 2A and 2B. In FIG. 2I, the index plotted is the ratio C2phen/Hopane; in FIG. 2J, the ratio C2phen/C3phen; and in FIG. 2K, the ratio is the Paraffin/Naphthene ratio from pumpdown data. In FIG. 2K, the plotted points represent the ratio of the two curves in FIG. 2A. The C2phen, C3phen and Hopane concentrations plotted in FIGS. 2I and 2J are obtained by passing the pyrolysis $S_1$ compounds through on a gas chromatographic column, which separates the individual components based on volatility. As the separated compounds exit the column, they are passed into a mass selective detector such as a mass spectrometer, where the C2phen, C3phen, and Hopane peaks are identified. All three graphs show the oil quality varying from the best quality (Grade A) at the shallower depths to the worst quality (Grade C) at the deeper depths near the oil-water contact 23. The degradation index from the present inventive method (FIG. 2K) compares favorably in a qualitative way to the indices obtained by more expensive and time consuming chemical analysis (FIGS. 2I and 2J).

FIGS. 2L, 2M and 2N further illustrate the performance of the present inventive method as an oil quality estimation tool. A known pyrolysis technique called Pyrolysis GCMS of the $S_1$ component is a standard oil quality measurement often used for oil-water contact determination and other quality degradation assessments. FIG. 2L shows the aromatic degradation index from PyGCMS($S_1$) analysis plotted against the Paraffin/Naphthene ratio using pumpdown data. The correlation between these two quantities is obvious from the graph, demonstrating that the Paraffin/Naphthene ratio is also an oil quality index. Similarly, FIGS. 2M and 2N show that the Paraffin/Naphthene ratio correlates with oil viscosity (FIG. 2M) and API gravity (FIG. 2N). The data for FIGS. 2L, 2M and 2N come from the heavy oil region of Canada.

FIG. 2P is similar to FIG. 2L. It confirms that the Paraffin/Naphthene ratio from the present inventive method is a valid oil degradation index by comparison to another accepted degradation parameter obtained by PyGCMS analysis (C2phen/[Hopanes+C2phen]). The discussion of the Paraffin/Naphthene ratio is not intended to limit the present inventive method, but instead is intended to be illustrative only. The pumpdown response spectrum may contain other peaks besides (m/z=55) and (m/z=57) that yield a ratio that reflects oil quality.

The pyrolytic and other chemical analysis methods mentioned in the preceding examples and test results will all be familiar to a person of ordinary skill in the art, and are explained in detail in many chemistry textbooks.

Figure 2Q:
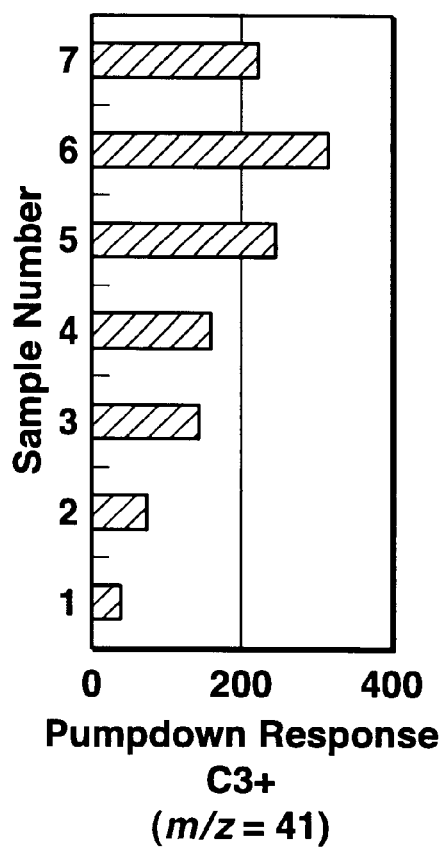
FIGS. 2Q and 2R illustrate use of the present invention to detect zones of high natural oil saturation against a background of drilling-introduced diesel contamination.
Figure 2R:
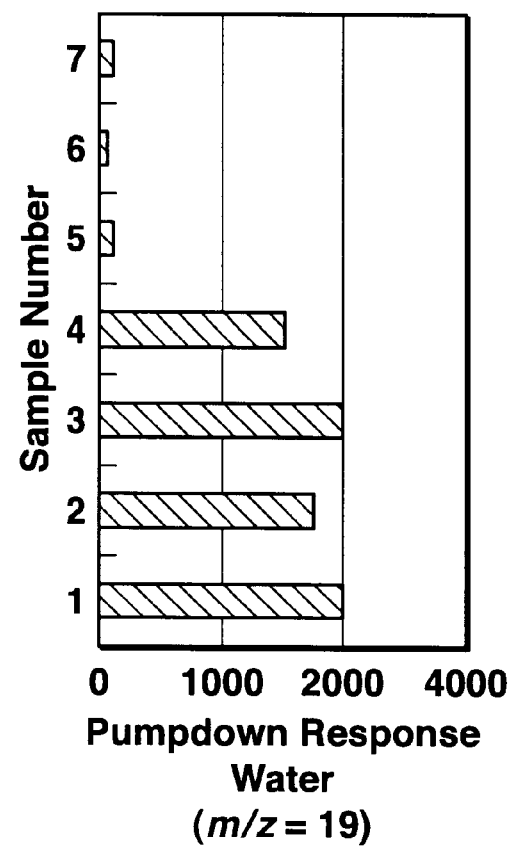

FIGS. 2Q and 2R illustrate use of the present inventive method on rock samples contaminated with oil-based drilling fluid, with the objective being to detect a zone with high natural oil saturation. Use of oil-based drilling fluids usually results in heavy hydrocarbon contamination of rock samples within a well. This contamination severely limits the ability to detect natural oil saturation using conventional geochemical tools. The present inventive method can be used to overcome this limitation. Core samples containing high oil saturation (samples 5, 6 and 7) and samples containing no oil (samples 1, 2, 3 and 4) were all artificially contaminated with diesel in the laboratory to simulate contamination during drilling with oil-based mud. Each sample was then analyzed using the present inventive method. The $C3^+$ peak (m/z=41) response is plotted in FIG. 2Q and the water peak (m/z=19) response is plotted in FIG. 2R. The combination of high $C3^+$ and low water responses can clearly be used to detect zones with high oil saturations. This technique is useful for identifying hydrocarbon migration zones and for detecting hydrocarbon-water contacts.

Figure 3:
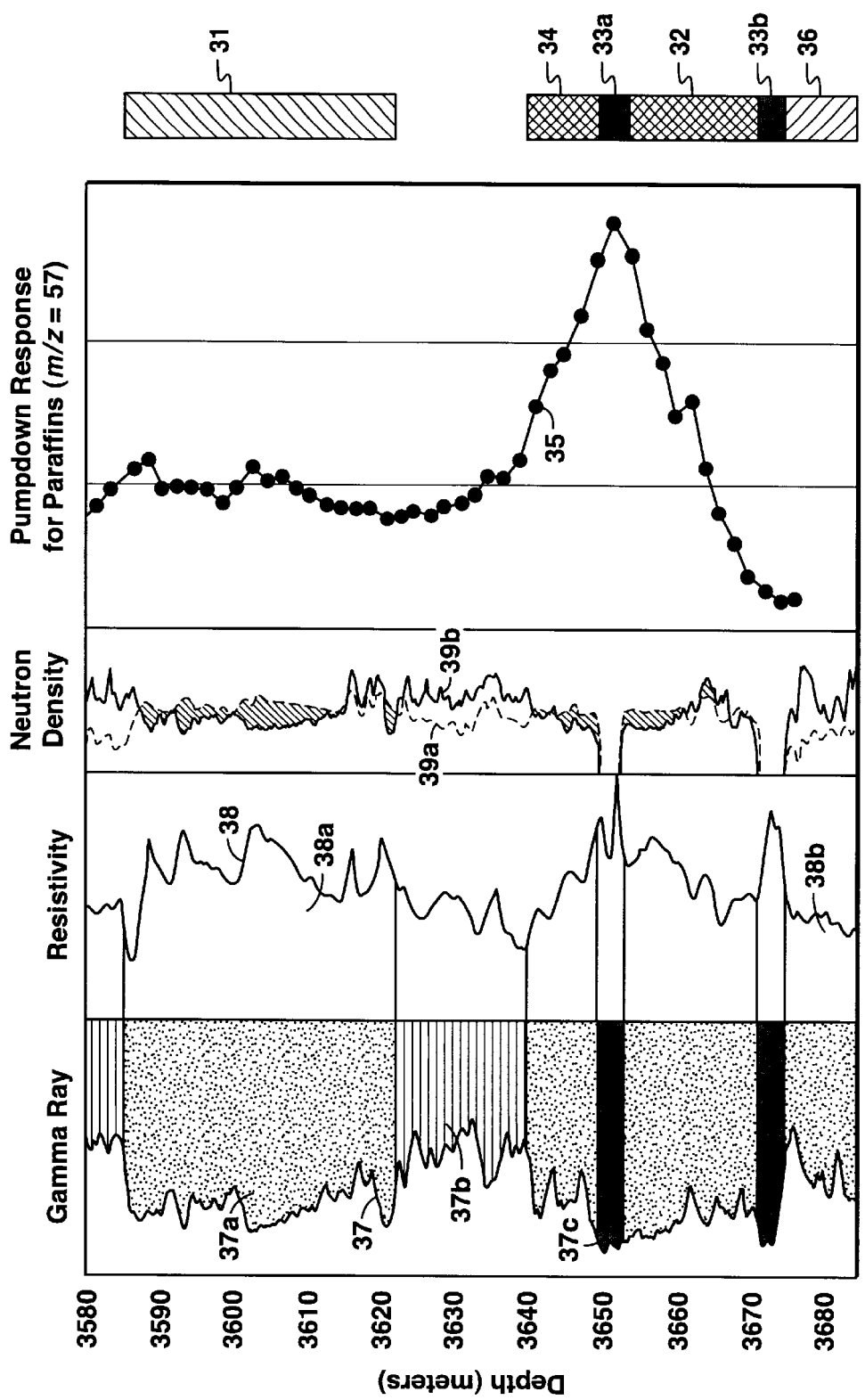
FIG. 3 illustrates the use of the present invention compared to conventional techniques in predicting hydrocarbon presence in an unknown zone.

FIG. 3 illustrates use of the present inventive method on core samples to predict presence of hydrocarbons and whether predicted hydrocarbons are oil or gas. The samples came from a well in a producing gas field. Gas is produced from a depth of about 3585 meters to 3622 meters, as indicated by 31. Oil was recovered from a drill stem test in a narrow zone 32 centered around 3,660 meters deep, with thin layers of coal 33a and 33b just above and below. Water was produced from zone 36. Either gas or oil was suspected at 34 just above the upper coal zone. The objective of this application of the present invention was (a) to confirm (in a predictive sense) hydrocarbons at about 3,645 meters (zone 34), and (b) to predict whether the hydrocarbons are oil or gas.

The results of a Gamma Ray log 37 taken in the well bore are shown in FIG. 3 as an example of a conventional technique used to determine rock type. The Gamma Ray log 37 can predict only whether reservoir rock exists (low readings) which could possibly contain hydrocarbons, or whether non-reservoir rock (high-readings) such as shale exists. The reservoir rocks such as 37a are shown in FIG. 3 with a stippled pattern while the non-reservoir rocks such as 37b are shown with a horizontal rule pattern. The non-reservoir coal horizons are also indicated in the same rock column display, with 37c denoting the upper of the two horizons. The resistivity curve 38 in FIG. 3 is used to distinguish those reservoir rocks containing hydrocarbons (high readings, for example 38a) from those with water in the pore spaces (low readings, for example 38b), but is incapable of differentiating gas from oil. FIG. 3 also shows a neutron porosity curve 39a on the left and a density porosity curve 39b on the right. Departures of the neutron curve to the right so that it "crosses over" the density curve (the shaded areas between 39a and 39b), are used to pick gas zones. However, for this example one can clearly see that the density/neutron crossover occurs in the known gas zone but also in the known oil and unknown zones. Therefore, standard logging tools suggest that there are hydrocarbons at 34, but one has no confidence in determining whether zone 34 contains gas or oil. The pumpdown data 35 from the present invention are also shown in FIG. 3, where paraffins (m/z=57) data are plotted. The relative response of the 57 peak is greater for oil than for wet gas. The key information conveyed by the pumpdown data is that zone 34 looks quite like zone 32, and very unlike zone 31. This prediction that zone 34 contains oil is in fact correct. The high pumpdown response of the upper coal layer (33a) is interpreted to be due to the migration of hydrocarbons into this relatively tight rock from the surrounding reservoirs. In general, the high pumpdown response from the oil leg, the intermediate response from the gas leg, and the low response from the water leg in this example is similar to FIG. 2A and could also be used here to pick the gas-oil and oil-water contacts.

The relatively low response at band 31 may be partly due to the age of the sample. These samples were about 20 years old, which may affect retention of the lighter volatiles (gas) more than the heavy volatiles (oil).

Figure 4:
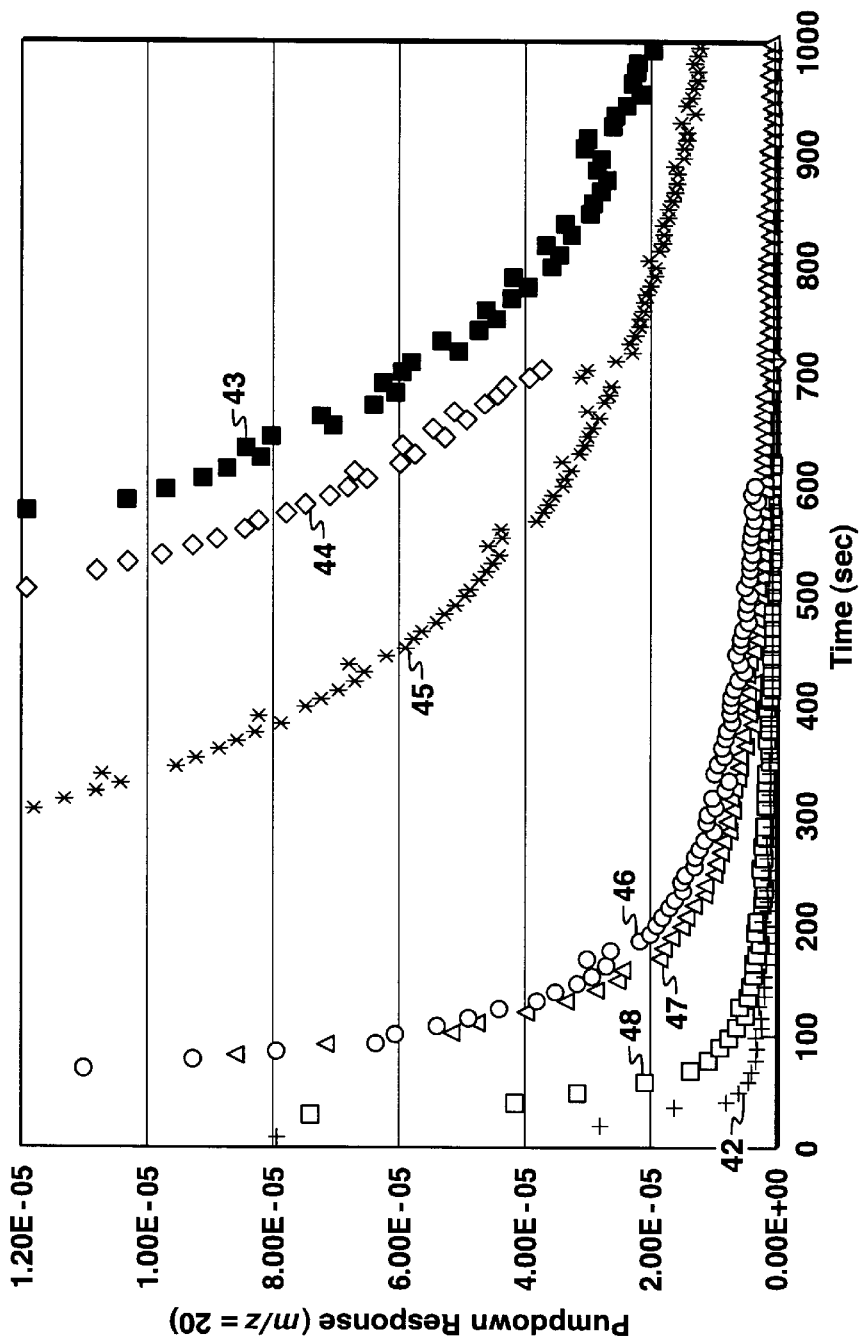
FIG. 4 illustrates use of the present invention to estimate permeability of a rock sample by interpolation between results for samples of known permeability.

FIG. 4 illustrates use of the present inventive method to estimate rock properties. Cuttings of known permeability were ground and sieved to produce one-gram samples of $\geq 1$ mm in size. Each sample was analyzed using the present inventive method, and the water peak (m/z=20) response is plotted as a function of time. This application of the present invention is to be contrasted with that used for FIG. 2C or FIG. 3, for example. In those two cases, the numbers shown for a chosen m/z peak represent an integral count over the entire data collection time, on the order of 80 seconds or less. For permeability estimations such as FIG. 4, the numbers plotted represent differential count rates, collected over time for a much longer total period of time. What is actually plotted in FIG. 4 as a function of time is the ion current (m/z=20) which is proportional to the instantaneous count rate. The count rates fall off as a function of time (when they were collected). The vacuum pump is kept operating throughout. The curves lie in a sequence following the sample's permeability value, such that the curves for higher permeability rocks decline more steeply than the curves for low permeability rocks. Curve 43 represents a sample with permeability of 0.74 milliDarcy, curve 44 a 1.1 mD sample, curve 45 a 41 mD sample, curve 46 a 143 mD sample, curve 47 a 231 mD sample and curve 48 a 753 MD sample. The value of a plot such as FIG. 4 will be obvious to persons of ordinary skill in the art. A sample of unknown permeability can be analyzed and plotted in the same way. Its permeability may be estimated by interpolation from the standardized curves of known permeability. This procedure is much simpler than known methods for measuring permeability and can be performed on cuttings. Other ways of plotting the data to generate families of curves for interpretation purposes, such as integral count rate vs. time, may alternatively be used. Also, other peaks besides the water peak may be used. All that is required is a molecule that resides in significant quantity in the pore spaces of the sample at the time of analysis.

Any molecule that is present in the pumpdown gases in reasonable abundance can be used for purpose of rock property estimations. Water is a good choice because it is almost always the strongest signal. The data of FIG. 4 was collected using a mass spectrometer with a low-resolution probe. The resolution was adequate because of the strength of the water signal.

Figure 5:
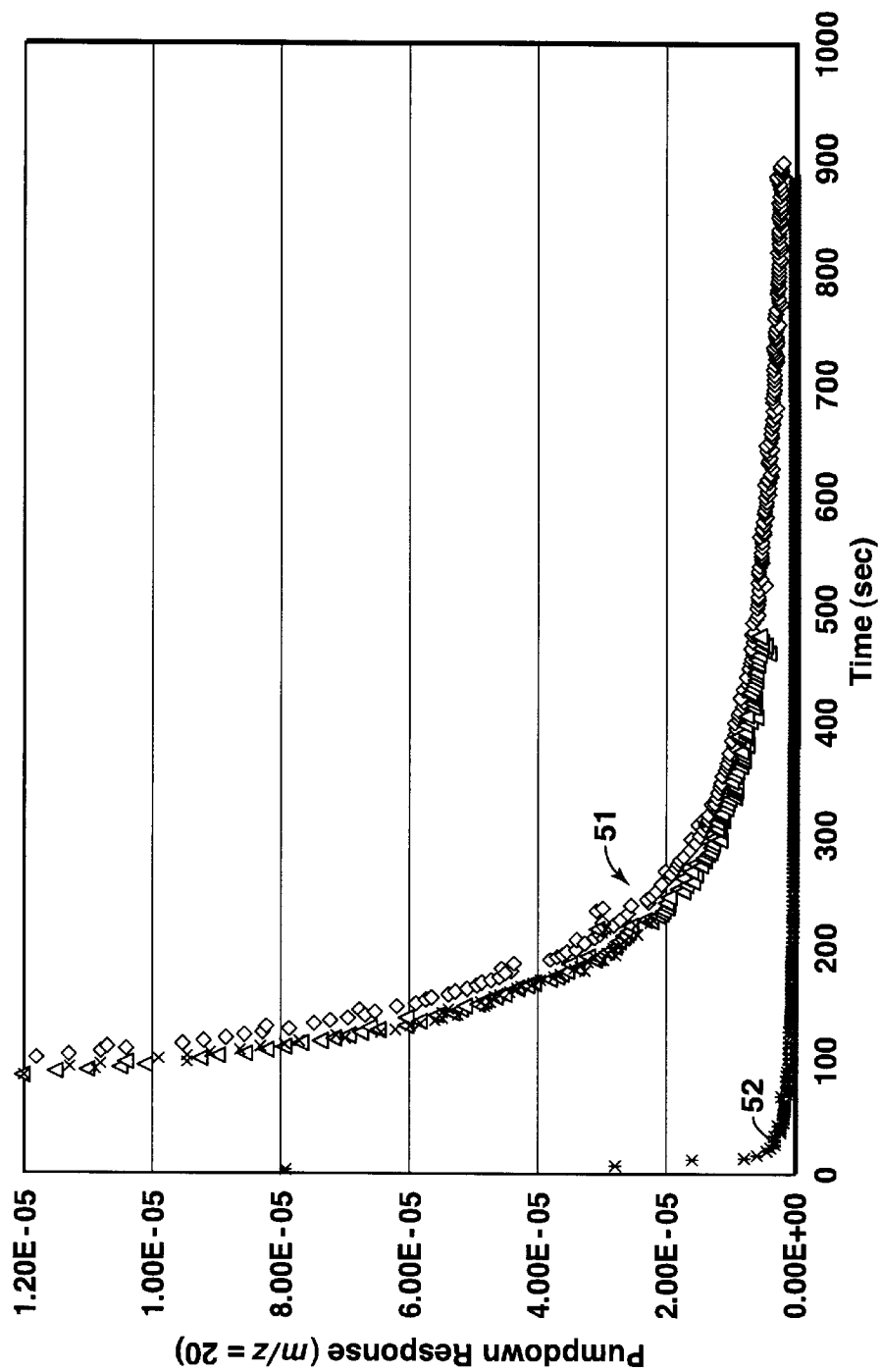
FIG. 5 illustrates data reproducibility for an application similar to that of FIG. 4.

FIG. 5 demonstrates the excellent reproducibility of measurements of the type used to generate FIG. 4. Three samples, identically prepared from the same crushed core, are separately analyzed and the results are the curves 51. The spread is small, indicating good data reproducibility. The curve 52 represents pumpdown data taken with no sample in the chamber to measure background, and similarly with curve 42 in FIG. 4.

Figures 6A, 6B, 6C, 6D:
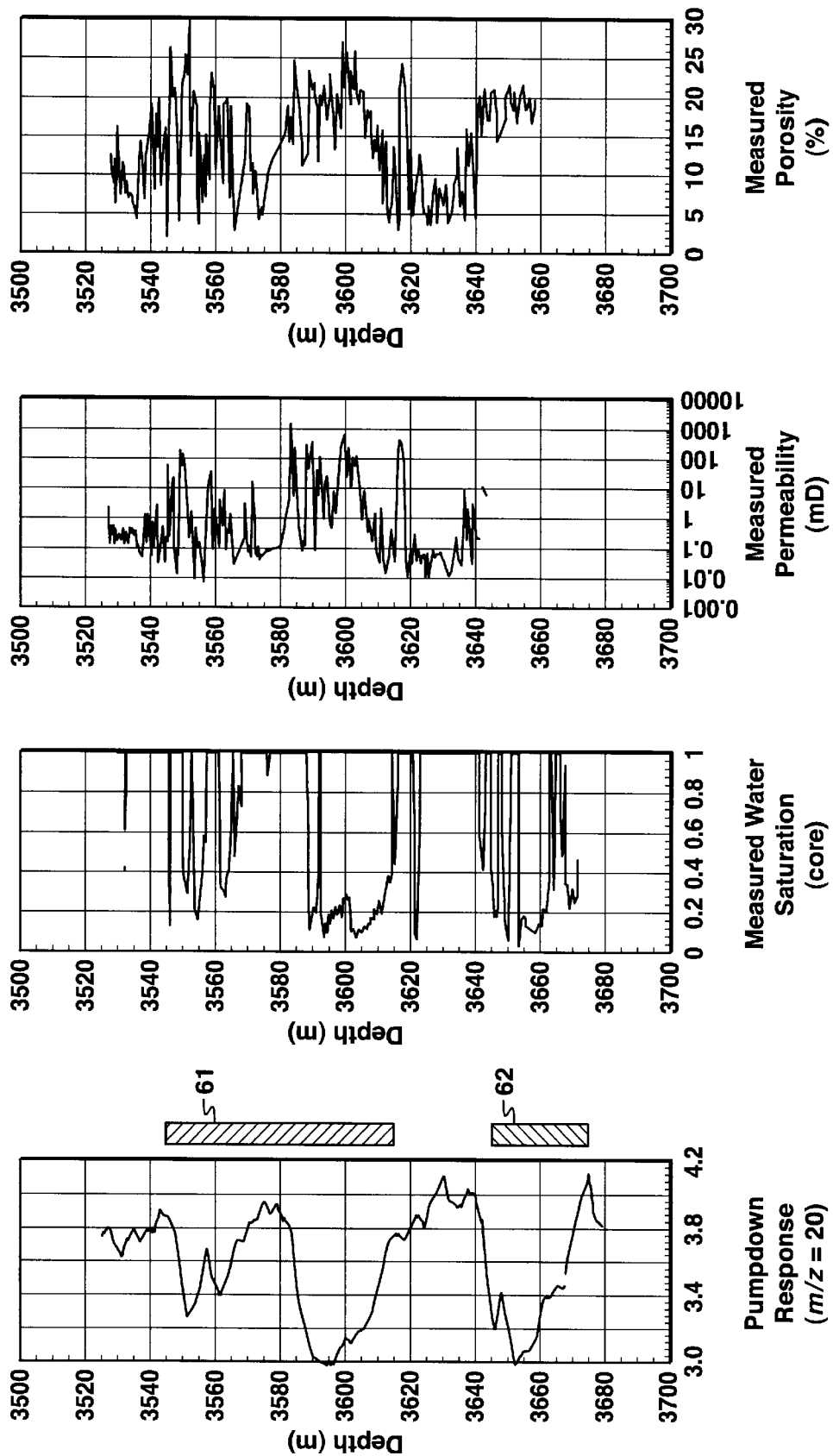
FIGS. 6A–6D illustrate use of the present invention to estimate another rock property, water saturation.

The approach of FIG. 4 can be used to estimate other rock properties such as porosity. The rock property "water saturation", defined as percent of the available pore space that is filled with water, can also be estimated by the same approach. Furthermore, the approach of FIGS. 2C and 3 can also be used to show concentration of water, rather than petroleum indicators, as a function of depth. The correlation between the pumpdown response for water (m/z=20) in FIG. 6A, and the measured water saturation of the core samples in FIG. 6B, is quite close. The samples are from the same well that yielded the data in FIG. 3, with a gas zone 61 at about 3,545–3,615 meters and an oil (plus coal) layer 62 at about 3,645–3,675 meters. The low responses for water correlate with the presence of petroleum. Thus, water also can be an indirect hydrocarbon indicator in the present inventive method. FIGS. 6C and 6D show the measured permeability and porosity as a function of depth. Water saturation requires knowledge of the porosity, and sufficiently high permeability is required to produce hydrocarbons from the rocks. Low water saturation combined with high porosity and permeability are the most favorable properties from the standpoint of petroleum exploration. The measurements in FIGS. 6B, 6C and 6D were all performed by conventional techniques, all of which are more time consuming and expensive than the pumpdown analysis of the present invention.

Figure 7:
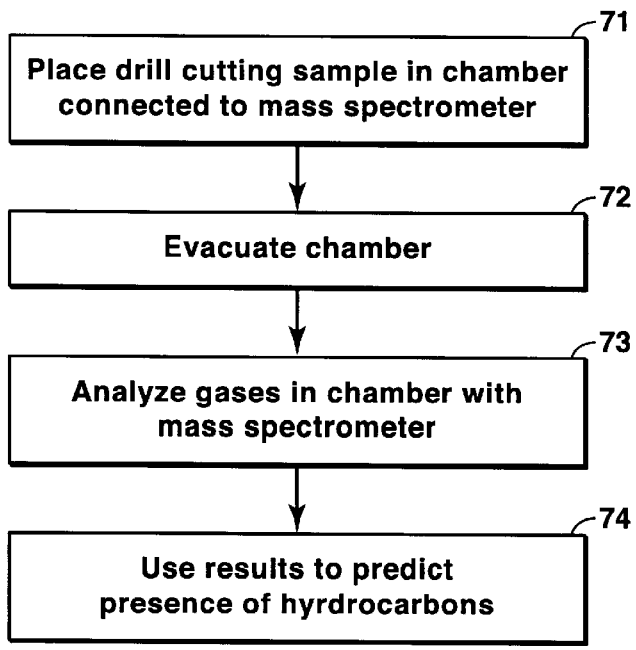
FIG. 7 is a flowchart illustrating the basic steps of some embodiments of the present inventive method, directed toward predicting hydrocarbon presence or to distinguishing gas zones from oil zones and water zones.
Figure 8:
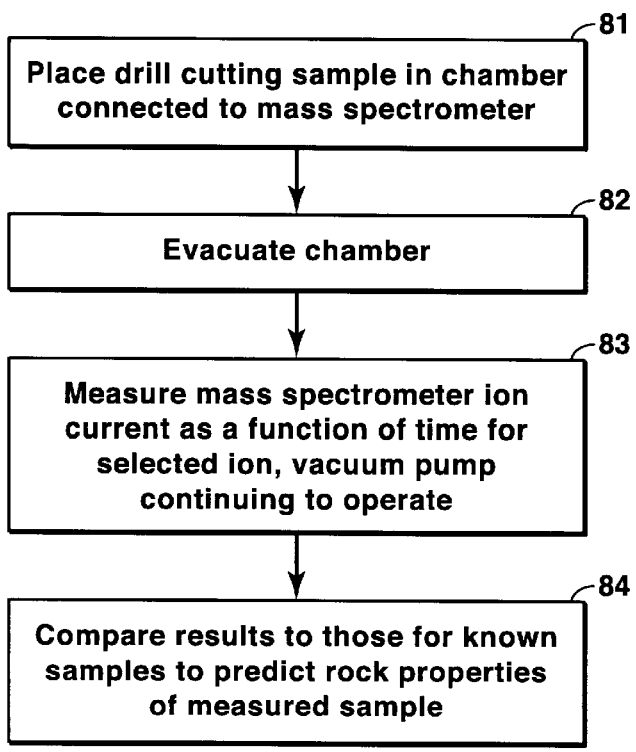
FIG. 8 is a flowchart illustrating the basic steps of some embodiments of the present inventive method applied to the estimation of rock properties.

The flow charts of FIGS. 7 and 8 may be used to summarize the two applications of the present inventive method that are discussed above. FIG. 7 illustrates one embodiment of the present invention for use in petroleum prospecting. At step 71, a sample such as a drill cutting, core or outcrop sample is introduced into an airtight chamber that is already under vacuum, or is then evacuated, or both. At step 72, the chamber is further evacuated if necessary until a sufficiently high vacuum is reached such that a mass spectrometer can be operated. This initial pumping time can be pre-determined from experience for automated applications. At step 73, a mass spectrometer is used to analyze the gases in the chamber, which will include gases that were adsorbed to the surfaces or trapped in the pore spaces of the sample. At step 74, the user looks at the concentrations for m/z values known to be petroleum indicators, and draws conclusions about existence of hydrocarbons or water and possibly the question of oil vs. gas in the zone from which the sample came.

Refinements to the above-described procedure will be obvious to those trained in the art. For example, multiple stages of vacuum may be used. In one example of this, the mass spectrometer chamber may be isolated from the sample chamber by a valve, with the sample chamber pumped by a roughing pump capable of approximately $10^{-2}$ torr. After the sample is inserted, by automation or by hand, into the sample chamber, and the chamber sealed, the roughing pump is given on the order of 10 seconds before the valve connecting to the mass spectrometer is opened. Analyzing may begin immediately in a typical scenario. It is often convenient to put the sample in an unsealed sample vial or container. The analysis procedure may be done on the empty vial to obtain a background reading that can be subtracted from the sample reading.

In the course of analyzing for a period such as 10 seconds in the preceding example, each m/z peak may be counted several times as the mass spectrometer is operated to scan through the range of m/z values and then repeat. The quantity directly measured by the mass spectrometer is ion current in milliamperes. Displays such as FIG. 2C or FIG. 3 are most conveniently made by showing for each sample and depth the measured ion current for the selected m/z value. Typically, the current value selected (from among the many recorded values) might be the peak value. Alternatively the value at a particular time after analyzing began might be used for all samples. Or the current readings might be summed for the entire analysis period (10 seconds per sample in the preceding example). Although experience shows that ion currents usually peak at different times for different values of m/z, such effects do not seem to be significant for purposes such as those of FIG. 2C or 3, and therefore the ion current values that are plotted in such figures can be selected from the data collected in any of the above-described ways or in other similar ways.

In addition to functioning as a stand-alone analytical method, the present invention is also readily suitable to being performed as a preliminary step to FIS analysis of the sample, or in combination with other established techniques such as GC/MS where a gas chromatograph is used as the first stage before a mass spectrometer.

FIG. 8 illustrates one embodiment of the present invention as applied to determining rock properties of a sample. Steps 81 and 82 are the same as steps 71 and 72, respectively, in FIG. 7. At step 83, the mass spectrometer is turned on and the ion current is noted at intervals of approximately 10 seconds, so that a representation of ion current decline as a function of time can be obtained. For each sample, data might typically be collected for 30 minutes with the vacuum pump continuing to operate. The m/z=20 peak (water) is very useful for rock property determinations. At step 84, the data are plotted and compared to similar curves previously obtained for samples with known values of the rock property of interest. The rock property for the unknown sample may be estimated by interpolation. In some preferred embodiments of the present invention, samples for rock property measurements are prepared by crushing and sieving to obtain a particle size of 1–2 mm. One gram of such 1–2 mm fragments is placed into a closed vial and stored until ready to analyze at which time the sealed top of the vial is replaced by a permeable top and the vial is introduced into the sample chamber. An empty vial may be analyzed separately to determine background.

Throughout the foregoing description, and in the appended claims, terms such as "exploring" and "prospecting" are intended to include the entire range of activities from the earliest stages of hydrocarbon exploration to such later steps as appraising or delineating a known field or hydrocarbon-bearing area for such purposes as determining where to drill wells, what zones in which to complete drilling and attempt to produce, where the oil-water interface might be, and similar production and development issues. The present inventive method can be applied to make effective contributions to all of these activities.

As used in the claims, the term "vacuum pump" will be understood to refer to one or more stages employing one or more roughing pumps, turbomolecular pumps, diffusion pumps, molecular sieves, cryogenic pumps or any other practical means of creating a vacuum. Also, "exploring" for petroleum will be understood to include all field delineation and production determinations and well drilling decisions of all types.

The foregoing description is directed to particular embodiments of the present invention for the purpose of illustrating it. It will be apparent, however, to one skilled in the art that many modifications and variations to the embodiments and applications described herein are possible. For example, the sample could be heated to further assist the expulsion of the pore space and adsorbed fluids. Alternatively, samples could be separated into various carbon compounds using gas chromatographic or other methods prior to analysis by the present invention, or sample gases could be concentrated by any of a variety of means before analysis. Any detector that can make low-level particle concentration measurements and provide some indication of the fluid composition, i.e., which particular elements or compounds are being detected, may be used in place of the mass spectrometer in the present invention. Also, the present inventive method is equally suited to manual operation, automated computer-controlled operation, or any combination of those two approaches. All such modifications and variations are intended to be within the scope of the present invention, as defined in the appended claims.

We claim:

1. A method for exploring for petroleum in a subterranean region comprising the steps of:
    a) obtaining one or more samples from known locations in said subterranean region or on the surface thereof;
    b) placing a sample in an evacuated chamber connected to a detector capable of composition determinations and concentration measurements;
    c) using the detector to determine the compositions and measure the concentrations of fluids released by the sample due to the vacuum; and
    d) predicting the presence and location of petroleum in the subterranean region based on the measured concentration of petroleum indicator molecules.

2. The method of claim 1, wherein said samples are drilling cuttings.

3. The method of claim 1, wherein said samples are drilling core specimens.

4. The method of claim 1, wherein said detector is a mass spectrometer and molecular composition is inferred from the m/z ratio, where m is the molecular mass and z is the ionization charge.

5. The method of claim 1, wherein said petroleum indicators comprise at least one of the following: methane, ethane, paraffins, naphthenes, $C3^+$, alkylated naphthenes, benzene, and toluene.

6. A method of estimating at least one rock property of a rock sample comprising the steps of:
    a) placing the sample in an evacuated chamber connected to an operating vacuum pump and a detector capable of composition determinations and concentration measurements;
    b) using the detector to measure detection rate, as a function of time elapsed since the beginning of such data collection, for at least one molecular constituent of the adsorbed and interstitial fluids released by the sample due to the vacuum; and
    c) estimating a desired rock property value for said sample by comparing the results from step (b) with similarly obtained results from other samples with known values of said rock property.

7. The method of claim 6, wherein the rock property thus estimated is permeability.

8. The method of claim 6, wherein the rock property thus estimated is porosity.

9. The method of claim 6, wherein the rock property thus estimated is water saturation.

10. The method of claim 6, wherein the molecular constituent is water.

11. The method of claim 6, wherein the detector is a mass spectrometer.

12. A method for exploring for petroleum in a subterranean region comprising the steps of:
    a) obtaining one or more samples from known locations in said subterranean region or on the surface thereof;
    b) placing a sample in an evacuated chamber connected to a detector capable of composition determinations and concentration measurements;
    c) using the detector to determine the compositions and measure the concentrations of adsorbed and interstitial fluids released by the sample due to the vacuum; and
    d) predicting the presence and location of petroleum in the subterranean region based on the measured concentration of petroleum indicator molecules.

13. A method for estimating the quality of oil contained in a sample, comprising the steps of:
    a) placing the sample in an evacuated chamber connected to a detector capable of composition determinations and concentration measurements;
    b) using the detector to determine the identities and concentrations of the constituents of the adsorbed and interstitial fluids released by the sample due to the vacuum;
    c) selecting a first constituent known to be more abundant in high quality oil than in low quality oil, and a second constituent known to be more abundant in low quality oil than in high quality oil; and
    d) combining the concentration of the two selected constituents to yield a parameter representative of the quality of the oil in the sample.

14. The method of claim 13 wherein said parameter is the paraffin concentration divided by the naphthene concentration.

15. A method for estimating oil quality and the oil-water contact depth from samples taken from varying depths in a well or core, comprising the steps of:
    a) placing a sample in an evacuated chamber connected to a detector capable of composition determinations and concentration measurements;
    b) using the detector to determine the compositions and measure the concentrations of the adsorbed and interstitial fluids released by the sample due to the vacuum;
    c) repeating steps (a) and (b) for each sample; and
    d) comparing the samples with respect to their concentration for water and for a selected petroleum constituent and using these comparisons to estimate oil quality as a function of depth, and thereby to estimate the depth of the gas-oil or oil-water contact.

16. A method for exploring for petroleum in a subterranean region comprising the steps of:
  a) obtaining one or more samples from known locations in said subterranean region or on the surface thereof;
  b) placing a sample in a chamber connected to a vacuum pump and to a detector capable of composition determinations and concentration measurements;
  c) evacuating the chamber;
  d) using the detector to determine the compositions and measure the concentrations of fluids released by the sample due to the vacuum; and
  e) predicting the presence and location of petroleum in the subterranean region based on the measured concentration of petroleum indicator molecules.

* * * * *

UNITED STATES PATENT AND TRADEMARK OFFICE
CERTIFICATE OF CORRECTION

PATENT NO. : 6,661,000 B2
DATED : December 9, 2003
INVENTOR(S) : Michael P. Smith et al.

It is certified that error appears in the above-identified patent and that said Letters Patent is hereby corrected as shown below:

<u>Title page,</u>
Item [54], Title, should read -- METHOD FOR MEASURING ADSORBED AND INTERSTITIAL FLUIDS -- instead of "METHOD FOR MEASURING ABSORBED AND INTERSTITAL FLUIDS"

Signed and Sealed this

Sixth Day of July, 2004

JON W. DUDAS
*Acting Director of the United States Patent and Trademark Office*